United States Patent [19]

Lewis et al.

[11] 4,423,152

[45] Dec. 27, 1983

[54] EFFLUENT DETECTION METHODS

[75] Inventors: David F. Lewis, Monroe; Edward J. Kaplin, Stamford, both of Conn.

[73] Assignee: York Research Corporation, Stamford, Conn.

[21] Appl. No.: 271,650

[22] Filed: Jun. 8, 1981

[51] Int. Cl.$^3$ ...................... G01N 31/12; G01N 33/00
[52] U.S. Cl. ........................................ 436/56; 436/81; 436/155
[58] Field of Search ................... 23/230 PC, 230 HC; 436/56, 81, 155

[56] References Cited

U.S. PATENT DOCUMENTS 3,574,550  4/1971  Scott et al. .................... 23/230 HC
3,979,503  9/1976  Kaartinen ..................... 23/230 PC

OTHER PUBLICATIONS

Shum et al., J. of the Air Pollution Control Ass., vol. 25, No. 11.

Primary Examiner—Michael S. Marcus
Attorney, Agent, or Firm—William G. Rhines

[57] ABSTRACT

Methods and compositions of matter are disclosed, useful in detecting the source of particulate, gaseous borne effluents, comprising lanthanides which may be introduced into combustion processes. Sources may thereby be identified from the analytical responses of effluent particles as compared to those predicted for the introduced lanthanides which have been subjected to the known combustion conditions at the source.

7 Claims, No Drawings

EFFLUENT DETECTION METHODS

BACKGROUND OF INVENTION

Recent years have seen increased interest in environmental and pollution control. In this connection, frequently, it is desired to trace the origin of effluent materials. Thus, for example, it may be desired to identify factories and other sources of gaseous borne particulate pollution, such as those commonly referred to as smoke, aerosols, hazes, mists, and "smog". This may be of particular interest for example, as to electric or steam power generating plants, incinerators, or the like, burning wood, oil, gas, coal, synthetic fuel, processed or raw garbage, sewage sludge or refuse-derived fuels, and/or where several sources are so close to each other that their smoke or other gaseous particulate effluents are co-mingled, and it is desired to identify exactly which source among several is of particular interest. For example, one industrial plant in a group may be emitting particularly noxious, poisonous, otherwise objectionable materials as a combustion by-product, as a result of a process leak, or otherwise, and for policing purposes it is desired to identify exactly which among several sources having similar effluents is the source. Conversely, one source among several may wish to establish that it is not the origin of offensive constituents. Environmental considerations aside, it may simply be desired to achieve other results, such as monitoring a specified source for production efficiency. Another related area of interest is in tracing the atmospheric movements of specific air masses, per se as well as insofar as they may be carriers of such particulate pollutants.

It has been proposed to use radioactive materials for the positive tracing of sources in such situations, but these are now generally disapproved because, although they survive the combustion process itself, there is increased awareness of the dangers of the indiscriminate exposure of humans and other living things to radiation.

Accordingly, it is an object of this invention to provide means to trace the source of the gaseous borne particulate matter.

Another object of this invention is to provide such means in a manner which may be identified with its source.

Yet another object of this invention is to provide such means without disbursing radioactive materials.

SUMMARY OF INVENTION

Desired objectives may be achieved through the practice of this invention wherein combinations are made of materials, each of which exhibits elemental characteristics which are analytically identifiable that are different from those of the others, and each of which exhibits a predictable change in characteristics as a result of combustion, whereby gaseous effluent sources may be doped and the effluent when it is filtered and the filtrate is subjected to elemental analytical identification processes, will exhibit characteristics of the doping constituents in proportions with respect to each other as in the original doping material, adjusted for the predicted combustion-induced changes in characteristics of each.

DESCRIPTION OF PREFERRED EMBODIMENTS

The existence of the so-called "rare earth" elements has been known for some time. The designation "rare" stems from their having originally been discovered in scarce materials, and the designation "earth" from their having first been isolated in the form of "oxides", the chemical terminology of which is "earth". In fact, it is now known that this group is abundant in the earth's material. This group of elements are sometimes referred to as the "lanthanides" after lanthanum, their first member in the table of elements. Further, they are often treated as a separate branch in the table of elements and are sometimes known as the "fraternal fifteen" because of the great similarities to each other in physical and chemical properties which they display. Their exact characteristics have been catalogued in the technical literature (in this connection, see *Van Nostrand's Scientific Encyclopedia*, Fifth Edition, 1976, Van Nostrand Reinhold Company, New York, page 1996 et seq., and *Basic Inorganic Chemistry*, John Wiley & Sons, Inc., New York, 1976, at page 204, 219, and 447–455).

"The rare earth elements possess nearly identical chemical and physical properties and form a geo chemically coherent group. It is well known that the abundance relationship between rare earth elements exhibits a very unique pattern. Namely, the rare earth element of even atomic number is more abundant that that of the adjacent odd atomic number (Oddo-Harkins rule). In addition, the abundances of even atomic number (or odd atomic number) elements decrease approximately linearly with increasing the atomic number. The rare earth elements are usually sufficiently coherent to preserve this general abundance-relationship pattern. However, the pattern varies somewhat in different rocks and soils. The abundance-relationship pattern in the atmosphere should reflect the relative abundance of various types of rocks in the vicinity of the sampling site. The rare earth elements are expected to be a suitable natural indicator to determine the origin, behavior and fate of crustal aerosol in the atmosphere". (Sugimae, Akiyoshi (1980). Atmospheric Concentrations and Sources of Rare Earth Elements in the Osaka Area, Japan, ATMOS. ENVIRON, 14, 1171–1175).

The fact that the rare earth elements occur naturally, albeit in reduced concentrations, and are not radioactive, have made them of interest for use in tracer applications, and some work has been done so utilizing such materials. In this connection, reference is made to the *Journal of the Air Pollution Control Assocation*, Vol. 25, No. 11 for November, 1975 Article entitled "The Use of Artificial Activable Trace Elements to Monitor Pollutant Source Strengths and Dispersal Patterns" by Shum et al pg. 1123 et seq., where it is proposed to spray pollutant sources with solutions of compounds of the rare earth elements and monitor detected concentrations against the natural background level of the elements used. It is important to notice, however, that such teachings do not envision combining the tracer material directly with the source material that is being traced, but rather merely associating the tracer materials with the fluid phase with which the source material is associated. By virtue of this difference, with the present invention, the tracer is directly and intimately associated with the source material, and therefore the two are not subject to dispersion independent of each other or intrusions from other sources with the aberrations which they might produce. Instead, the particles of source materials continue to be readily identifiable as "un-natural natural" particles, i.e., ones exhibiting extraordinary levels of natural "rare earth" characteristics, whether per se or in "artifact" form which results from a subsequent reaction that creates a different compound. So far as is known, the present invention is the first disclosure of the use of rare earth elements for directly doping combustible material, in regulated proportions so as to facilitate identification on a comparative, rather than a quantitative basis, and to ensure direct identification with the combused material without possible intervention from another source, substantially irrespective of what happens to it later on.

In summary, the lanthanide series may be described as having unique properties, as being of substantially uniform abundance geologically as a function of atomic number, of having a substantially fixed abundance relative to one element (lanthanum), and of maintaining substantially the same ratio of abundance upon combustion, relative one to the other, even though changed in compound form and quantity by the process.

The lanthanides are known to occur naturally in fuels, such as coal, although the foregoing relationships sometimes do not remain valid as to natural occurance in some liquid fuels such as oils. Nevertheless, the lanthanides may be introduced into the liquid fuels in the form of soluble compounds, an example being the utilization of lanthanide stearates dissolved in fuel oil. Because of these factors, and the similarity of their behavior chemically and physically as between elements in the group, the lanthanides lend themselves particularly to utilization in combustion process monitoring since they tend to react to combustion substantially predictably as compared to each other as well as in comparison to the "background" of such materials naturally present in commonly used fuels. These factors may be utilized in using such materials in particular as effluent tracers in accordance with the teachings of this invention. For example, given the above-mentioned abundance alternations according to atomic number, it is possible to dope a fuel with a high amount of an element which is in low abundance naturally in the particular fuel in question, and to use detection of this artificially induced irregularity in the particulate effluent as a means to trace to the fuel source so doped. Similarly, it is possible to introduce two or more such elements in known proportions with respect to each other and, being able to predict the change in each which the given combustion process will induce to monitor effluents for detection of the ratio of elements so changed. The advantage of using the lanthanides two or more at a time is that each will be similarly affected by the conditions of the combustion process and therefore the ratio of the two or more lanthanides will be substantially the same in the effluent as it is in the fuel. The analyses of the fuels and the emission products for the requiste constituent lanthanide elements may be accomplished by any of a variety of analytical techniques obvious to those skilled in the art. Such monitoring may be by any of a variety of known per se methods or procedures, such as scanning electron microscopy.

The practice of this invention may be with respect to emissions from a given source that is a relatively long distance away. Thus airborne material emanating from the emission source may be collected at distances varying between a few feet from the source to several miles from the source, and typically from several hundred feet to several miles. Samples may also or alternatively be collected directly from within the physical equipment or unit which is the emission source. Emission from a source may be monitored by the collection of samples of material directly as they emanate from that source. While this data alone may be of limited use in tracing the effect of emissions over large distances or areas, it serves to demonstrate that the lanthanides exhibit properties useful in the practice of embodiments of this invention. Thus, when a fuel oil is homogeneously doped with some ratio of two or more lanthanide elements in compound form, the particulate matter emanating from that combustion process also contains those same lanthanide elements in substantially the same ratio to each other as they were present in the fuel oil.

In order to demonstrate the effectiveness of a lanthanide doped fuel oil for use as a tracer, selected prepared combinations were test-fired in a household heater furnace designed to fire No. 2 fuel oil at a rate of between 1.0 to 1.5 gallon per hour. The furnace was adapted to provide a sampling port in its exhaust duct and also to allow for a separate, isolated entry into the fuel line just upstream of the fuel pump.

A sample probe was created of sufficient length to allow for the dissipation of heat of the flue gas from approximately 1400° F. to less than 250° F. This latter temperature was sufficient to maintain the integrity of Millipore Type AA, 0.8 microns pore cellulose acetate membrane filters. One end of the sample probe was placed into the sample port in the furnace exhaust duct such that the open end of the probe faced directly into the exhaust gas stream. The sample probe was connected to a manifold capable of splitting the gas flow into two equal portions. Each arm of the manifold was fitted with a 47 mm diameter filter, one holding a glass fiber filter and the other holding a Millipore Type AA, 0.8 microns pore celluose acetate membrane filter. The flow rate through each filter assembly was controlled by a critical orifice. Flow of flue gas through the system was established by connecting the output side of the filters to a diaphragm pump creating a vacuum of 18 inches of mercury. The nominal flow rate through each filter assembly was 14 liters/min.

Prior to the beginning of each test, the filter assemblies were loaded with a fresh filter of each type (i.e. a millipore 0.8 micron pore cellulose acetate filter and a glass fiber filter). The fuel reservoir was drained of fuel from a previous test run, and then filled with the doped No. 2 fuel oil test mixture. The furnace was turned on and was permitted to become acclimated for at least 5 minute acclimatization burn, the diaphragm vacuum pump was activated and the flue gas sample was passed through the filter assemblies. Flue gas sampling was continued for 15 minutes, the fuel consumption being approximately 45 ml/min. during this period. The sample fuel reservoir was recharged as necessary during the test burn period.

After the vacuum diaphragm pump had been turned off and effluent gas sampling was complete, it was usual to allow the furnace to run until the residual fuel sample in the reservoir and fuel supply lines had been burned off. For each test, the doped No. 2 fuel oil and the glass fiber filter were analyzed by an inductively coupled argon plasma technique for the appropriate lanthanide elements and the ratio of those elements input to and output from the burner system was calculated. The particles accumulated in the Millipore filters were analysed by the technique and also with apparatus known as energy dispersive X-ray, electron probe microanalysis ("EDM"), and the results of those analyses produced substantially the same results of obtained with the glass fiber filters.

It is to be understood that this invention does not require absolute quantitative analysis for each element with regard to the doped fuel sample and the glass fiber filter. Since only the ratio of the elements is desired, it will be obvious to those skilled in the art that the handling transfer and dilution of the samples during analysis need not be upon a strict quantitative basis, as would apply if one were interested in obtaining an absolute analysis. In a sense, each sample (doped fuel oil or filter) has an internal standard reference point so long as the conditions pertaining to the samples and their analyses do not cause the separation of the various lanthanide tracer elements.

The following examples will serve to illustrate the utility of this invention.

EXAMPLE 1

Gadolinium stearate and dysprosium stearate powders were mixed in approximately 2:1 ratio and about 5 grams of the mixture was dissolved in 100 ml of warm o-xylene to furnish a clear stock solution. To 1 gallon of No. 2 fuel oil was added, with stirring, sufficient stock solution to provide a doped fuel oil containing approximately 10 ppm of dopants (based upon metal). The doped fuel oil was burned in the test unit previously described and exhaust gas was sampled through a glass fiber filter. Analysis of the doped fuel oil showed that the ratio of gadolinium to dysprosium was 2.2:1. The glass fiber filter sample contained gadolinium:dysprosium in the ratio 2.4:1. Since these ratios are well within the error of analysis it is concluded that the output from the burner may be distinguished by the ratio of gadolinium:dysprosium in the fuel.

A sample of undoped fuel oil did not contain any detectable amount of gadolinium or dysprosium. A blank filter contained no detectable amount of dysprosium, while the amount of gadolinium (0.09 ppm) was slightly higher than the detection limit (0.5 ppm).

EXAMPLE 2

Oil soluble compounds of lanthanum and of dysprosium were dissolved in an aromatic hydrocarbon solvent to provide an approximately 10% stock solution containing lanthanum:dysprosium in approximate ratio 1:2. The stock solution was added to 1 gallon of No. 2 fuel oil to provide a doped fuel containing approximately 10 ppm of dopants.

When tested in a manner similar to that described in Example 1, it was found that the doped fuel oil and the effluent gas contained the elements lanthanum and dysprosium in the ratios 1:2.0 and 1:2.1 respectively. Undoped fuel oil contained no detectable amount of either lanthanum or dysprosium. A glass fiber filter used during the burning of undoped fuel oil contained no detectable amount of lanthanum or dysprosium.

The ratios 1:2.0 and 1:2.1 are not distinguishable by view of the error in analysis and it is concluded that the output of the burner may be distinguished by the ratio of lanthanum and dysprosium in the fuel.

EXAMPLE 3

One gallon of doped No. 2 fuel oil was made by adding to fuel oil a stock solution containing lanthanum, dysprosium and gadolinium stearates dissolved in o-xylene. The doped fuel oil contains approximately 10 ppm of the lanthanides in the approximate ratio lanthanum:gadolinium:dysprosium=0.5:1:1.5.

The doped oil was burned as described in Example 1 and the effluent gas sampled through a glass fiber filter. Analysis of the doped fuel oil prior to combustion showed it to contain lanthanum:gadolinium:dysprosium=0.50:1.00:1.60. The glass fiber filter contains these same elements in the ratio 0.50:1.00:1.50. Save for a barely detectable level of gadolinium on a control filter (0.09 ppm vs 0.05 ppm detection limit), no lanthanides were detected in a control experiment with undoped fuel oil.

EXAMPLE 4

Example 3 was repeated with the condition that the doped fuel oil contained about 100 ppm of the lanthanides. However, the results are essentially the same. Since ratios of lanthanum:gadolinium:dysprosium of 0.48:1.00:1.60 were detected on the glass fiber filter and 0.50:1.00:1.74 in the doped fuel oil. These ratios are the same within experimental error and demonstrate that this particular character of the effluent distinguishes the source by view of the fuel that it consumes.

In order that ready comparisons can be made, Table 1 has been constructed to show the analytical results for the appropriate combinations of doped fuel oils and filters.

TABLE I

| TEST # | Concentration in fuel oil, ppm | | | Concentration of Filter, ppm | | | Ratio in fuel oil | Ratio on Filters |
|---|---|---|---|---|---|---|---|---|
| | La* | Gd* | Dy* | La* | Gd* | Dy* | | |
| 2 | 0.10 | 1.00 | 0.45 | 0.10 | 0.51 | 0.21 | Dy:Gd 1:2.2 ± 0.3 | Dy:Gd 1:2.4 ± 0.3 |
| 3 | 0.96 | 0.05 | 0.47 | 0.57 | 0.09 | 0.27 | La:Dy 1:2.0 ± 0.4 | La:Dy 1:2.1 ± 0.4 |
| 4 | 0.27 | 0.50 | 0.79 | 0.22 | 0.43 | 0.59 | La:Gd:Dy 0.5 ± 0.1:1.0:1.6 ± 0.2 | La:Gd:Dy 0.5 ± 0.1:1.0:1.4 ± 0.2 |
| 5 | 2.50 | 5.10 | 8.90 | 1.20 | 2.50 | 4.00 | La:Gd:Dy 0.50 ± 0.03:1.0:1.74 ± 0.03 | La:Gd:Dy 0.48 ± 0.06:1.0:1.60 ± 0.06 |

*Error of detection:
La = ± 0.10 ppm;
Gd = ± 0.05 ppm;
Dy = ± 0.05 ppm

Inspection of the results displayed in Table I demonstrates that the particulate matter emanating from combustion of a sample of doped oil contains substantially the same ratio of lanthanide elements that were used to dope the oil.

It will be apparent from the foregoing that through practice of this invention, safe, effective and inexpensive means is provided to monitor gaseous-borne particulate matter which is the effluent of combustion. It will also be clear that the teachings herein presented may be applied as well in other fluid systems, with or without combustion per se as the diffusion means.

Accordingly, the embodiments herein disclosed and described are by way of illustration and not of limitation, and it is to be understood that this invention may be practiced in a wide variety of other embodiments without departing from the spirit or scope of this invention.

We claim:

1. A method of monitoring the gaseous, particle-bearing effluent of combustion, comprising the steps of combining with combustible material at least two tracer elements chosen from the lanthanide group in a predetermined ratio with respect to each other, subjecting said combination to combustion under said known conditions, gathering at least one sample of particles from gaseous effluent, determining by means of elemental analytical means the ratio, with respect to each other, of the responses of said sample corresponding to those exhibited by said tracer elements before they were combined with said combustible material, and comparing said ratio of responses of said sample to that of said tracer elements before they were combined with said combustible material.

2. The method described in claim 1 wherein said combining step comprises combining dysprosium and gadolinium with said combustible material.

3. The method described in claim 1 wherein said combining step comprises the step of combining with said combustible material dysprosium and gadolinium in weight ratio of about one part gadolinium to about two parts dysprosium.

4. The method described in claim 1 wherein said combining step comprises the step of combining with said combustible material dysprosium and lanthanum.

5. The method described in claim 1 wherein said combining step comprises the step of combining with said combustible material dysprosium and lanthanum in weight ratio of about one part lanthanum to about two parts dysprosium.

6. The method described in claim 1 wherein said combining step comprises the step of combining with said combustible material lanthanum stearate, dysprosium stearate and gadolinium stearate.

7. The method described in claim 1 wherein said combining step comprises the step of combining with said combustible material lanthanum stearate, dysprosium stearate and gadolinium stearate in weight ratios of about 0.5 to about 1 to about 1.5 of the lanthanum, dysprosium and gadolinium contents respectively.

* * * * *